(12) United States Patent
Schmitt et al.

(10) Patent No.: US 9,585,416 B2
(45) Date of Patent: *Mar. 7, 2017

(54) PREVENTING DISEASES IN INFANTS DELIVERED VIA CAESAREAN SECTION

(71) Applicant: N.V. Nutricia, Zoetermeer (NL)

(72) Inventors: Joachim Schmitt, Hoesbach (DE); Bernd Stahl, Utrecht (NL); Jan Knol, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/813,845

(22) Filed: Jul. 30, 2015

(65) Prior Publication Data

US 2015/0335053 A1 Nov. 26, 2015

Related U.S. Application Data

(63) Continuation of application No. 14/135,171, filed on Dec. 19, 2013, now Pat. No. 9,107,438, which is a continuation of application No. 12/091,011, filed as application No. PCT/NL2006/050247 on Oct. 6, 2006, now Pat. No. 8,715,769.

(30) Foreign Application Priority Data

Oct. 21, 2005 (EP) .................................. 05023029

(51) Int. Cl.
| | | |
|---|---|---|
| A23L 1/29 | (2006.01) | |
| A23L 1/30 | (2006.01) | |
| A61K 31/7016 | (2006.01) | |
| A23C 9/123 | (2006.01) | |
| A23C 9/20 | (2006.01) | |
| A61K 31/202 | (2006.01) | |
| A61K 31/702 | (2006.01) | |
| A61K 31/7068 | (2006.01) | |
| A61K 31/7072 | (2006.01) | |
| A61K 31/7076 | (2006.01) | |
| A61K 31/708 | (2006.01) | |
| A61K 31/732 | (2006.01) | |
| A61K 31/734 | (2006.01) | |
| A61K 35/745 | (2015.01) | |
| A61K 35/747 | (2015.01) | |
| A61K 35/74 | (2015.01) | |
| A61K 47/36 | (2006.01) | |
| A61K 31/7064 | (2006.01) | |

(52) U.S. Cl.
CPC .......... *A23L 1/3014* (2013.01); *A23C 9/1234* (2013.01); *A23C 9/203* (2013.01); *A23C 9/206* (2013.01); *A23L 29/065* (2016.08); *A23L 33/10* (2016.08); *A23L 33/12* (2016.08); *A23L 33/135* (2016.08); *A23L 33/17* (2016.08); *A23L 33/21* (2016.08); *A23L 33/40* (2016.08); *A61K 31/202* (2013.01); *A61K 31/702* (2013.01); *A61K 31/708* (2013.01); *A61K 31/7016* (2013.01); *A61K 31/7064* (2013.01); *A61K 31/7068* (2013.01); *A61K 31/7072* (2013.01); *A61K 31/7076* (2013.01); *A61K 31/732* (2013.01); *A61K 31/734* (2013.01); *A61K 35/74* (2013.01); *A61K 35/745* (2013.01); *A61K 35/747* (2013.01); *A61K 47/36* (2013.01); *A23V 2002/00* (2013.01); *A23Y 2220/85* (2013.01); *A23Y 2300/19* (2013.01); *A23Y 2300/21* (2013.01); *A23Y 2300/25* (2013.01); *A23Y 2300/29* (2013.01); *A23Y 2300/31* (2013.01); *A23Y 2300/41* (2013.01); *A23Y 2300/45* (2013.01); *A23Y 2300/49* (2013.01); *A23Y 2300/55* (2013.01); *A23Y 2300/59* (2013.01); *A23Y 2300/65* (2013.01)

(58) Field of Classification Search
CPC ......... A23C 9/1234; A23C 9/206; A23L 1/30; A23L 1/0345; A23L 1/296
USPC .................. 426/658, 43, 601, 656, 659, 801
See application file for complete search history.

(56) References Cited

U.S. PATENT DOCUMENTS

| | | |
|---|---|---|
| 4,994,442 A | 2/1991 | Gil et al. |
| 5,472,952 A | 12/1995 | Smidt et al. |
| 5,895,648 A | 4/1999 | Cavaliere Vesely et al. |
| 6,511,696 B2 | 1/2003 | Gohman et al. |
| 6,613,549 B2 | 9/2003 | Bruce et al. |
| 7,410,653 B1 | 8/2008 | Blareau et al. |
| 8,227,448 B2 | 7/2012 | Van Laere et al. |
| 2003/0022863 A1 | 1/2003 | Stahl et al. |
| 2004/0062758 A1 | 4/2004 | Mayra-Makinen et al. |
| 2004/0071824 A1 | 4/2004 | Van Laere et al. |
| 2004/0072791 A1 | 4/2004 | Kunz et al. |
| 2004/0072794 A1 | 4/2004 | Kaup et al. |
| 2004/0143013 A1 | 7/2004 | Schade et al. |

(Continued)

FOREIGN PATENT DOCUMENTS

| | | |
|---|---|---|
| EP | 0 847 244 B1 | 3/2001 |
| EP | 1 105 002 B1 | 7/2002 |

(Continued)

OTHER PUBLICATIONS

"La selection Udo Probiotiques: melange pour nourrissons," http://www.florahealth.com/flora/home/canadafr/products/TG8.htm#1966.

(Continued)

*Primary Examiner* — Helen F Heggestad
(74) *Attorney, Agent, or Firm* — Foley & Lardner LLP; Sunit Talapatra

(57) ABSTRACT

The present invention provides the use of a composition comprising non-digestible oligosaccharide for the manufacture of a composition for enteral administration to an infant delivered via caesarean section.

10 Claims, No Drawings

(56) References Cited

U.S. PATENT DOCUMENTS

| | | |
|---|---|---|
| 2006/0018890 A1 | 1/2006 | Isolauri et al. |
| 2006/0233773 A1 | 10/2006 | Herz et al. |
| 2007/0031537 A1 | 2/2007 | Secretin |
| 2007/0248649 A1 | 10/2007 | Sawatzki et al. |
| 2007/0274983 A1 | 11/2007 | Kluijtmans et al. |
| 2008/0199446 A1 | 8/2008 | Vriesema et al. |
| 2009/0162323 A1 | 6/2009 | Boehm et al. |
| 2011/0150851 A1 | 6/2011 | Schmitt et al. |

FOREIGN PATENT DOCUMENTS

| | | |
|---|---|---|
| EP | 1 364 586 A1 | 11/2003 |
| EP | 1 481 682 A1 | 12/2004 |
| EP | 1 597 978 A1 | 11/2005 |
| EP | 1 634 599 A1 | 3/2006 |
| WO | WO-98/06418 A1 | 2/1998 |
| WO | WO-00/08948 A2 | 2/2000 |
| WO | WO-00/08984 | 2/2000 |
| WO | WO-01/01785 A1 | 1/2001 |
| WO | WO-01/78530 A2 | 10/2001 |
| WO | WO-03/043445 A1 | 5/2003 |
| WO | WO-2004/032639 A1 | 4/2004 |
| WO | WO-2004/032651 A1 | 4/2004 |
| WO | WO-2004/067013 A1 | 8/2004 |
| WO | WO-2004/069156 A2 | 8/2004 |
| WO | WO-2004/093899 A1 | 11/2004 |
| WO | WO-2004/112507 A1 | 12/2004 |
| WO | WO-2004/112509 A2 | 12/2004 |
| WO | WO-2005/039318 A1 | 5/2005 |
| WO | WO-2005/039319 A1 | 5/2005 |
| WO | WO-2005/039319 A2 | 5/2005 |
| WO | WO-2005/039597 A2 | 5/2005 |
| WO | WO-2005/051088 A2 | 6/2005 |
| WO | WO-2005/110121 A1 | 11/2005 |
| WO | WO-2005/122790 A1 | 12/2005 |
| WO | WO-2006/087391 A1 | 8/2006 |
| WO | WO-2006/108824 A1 | 10/2006 |
| WO | WO-2006/115412 A2 | 11/2006 |
| WO | WO-2007/045502 A1 | 4/2007 |
| WO | WO-2007/046698 A1 | 4/2007 |

OTHER PUBLICATIONS

"Report of the Scientific Committee on Food on the Revision of Essential Requirements of Infant Formulae and follow-on Formulae," (2003) (See p. 63, 4th paragraph).
Artikel zum Thema, aid-infodienst-Ernahrung-Richtig Essennahrstoffempfehlungen, http://www.aid.de/eraehrung/naehrstoffempfehlungen_hauptnaehrstoffe.php (2010) pp. 1-5. (French Language).
Bakker-Zierikzee et al., "Effects of Infant Formula Containing a Mixture of Galacto- and Fructooligosaccharides or Viable Bifidobacterium Animalis on the Intestinal Microflora During the First 4 Months of Life," British Journal of Nutrition, 94:783-790 (2005).
Bennet et al., "Development of the Faecal Anaerobic Microflora After Caesarean Section and Treatment with Antibiotics in Newborn Infants," Infection, 15(5):332-336 (1987).
Bennet et al., "Transient Colonization of the Gut of Newborn Infants by Orally Administered Bifidobacteria and Lactobacilli," Acta Paediatrica, 81(10):784-787 (1992).
Bennet et al., "Fecal Bacterial Microflora of Newborn Infants During Intensive Care Management and Treatment With Five antibiotic Regimens," The Pediatric Infectious Disease Journal, 5(5):533-539 (1986) http://www.ncbi.nlm.nih.gov/pubmed/376418.
Bezirtzoglou E., "The intestinal Microflora During the First Weeks of Life," Anaerobe, 3:173-177 (1997).
Bezirtzoglou et al., "Apparition of Clostridium Sp. and Bacteroides in the Intestine of the Newborn Delivered by Cesarian Section," Comparative Immunology, Microbiology and Infectious Diseases, 13(4):217-221 (1990).
Bezirtzoglou et al., "Effect of the Feeding Practices on the Establishment of Bacterial Interactions in the Intestine of the Newborn Delivered by Cesarian Section," Journal of Perinatal Medicine, 17:139-143 (1989), Department of Microbiology, University of Ioannina, Ioannina, Greece, and Faculty of Pharmacy, Microbiology, University of Lille, Lille, France.
Bin-Nun et al., "Oral Probiotics Prevent Necreotizing Enterocolitis in Very Low Birth Weight Neonates," Journal of Pediatrics, 147(2):192-196 (2005).
Boehm et al., "Supplementation of a bovine milk formula with an oligosaccharide mixture increases counts of faecal bifidobacteria in preterm infants," Arch. Dis. Child Fetal Neonatal Ed., (2002), B6, pp. F178-F181.
Braunwald et al. (Editors), "Harrison's Principles of Internal Medicine," Eleventh Edition, McGraw-Hill Book Company, 502-503 (1987).
Bruzzese et al., "Early Administration of GOS/FOS Prevents Intestinal and Respiratory Infections in Infants," Journal of Pediatric Gastroenterology and Nutrition, 42(5):E95 (2006).
Calder et al., "Early Nutrition and Immunity—Progress and Perspectives," British Journal of Nutrition, 96:774-790 (2006).
Carver, D.J., "Advances in Nutritional Modifications of Infant Formulas," The American Journal of Clinical Nutrition, 77:1550S-1554S (2003).
Cibik et al., "Bacterial Intestinal Flora: Development, Characteristics and Influences of the Type of Feeding," Archives de Pediatrie, 11:573-575 (2004) (French Language).
Collins, et al., "Probiotics, Prebiotics, and Synbiotics: Approaches for Modulating the Microbial Ecology of the Gut," The American Journal of Clinical Nutrition, 69:1052S-1057S (1999).
Commission, "Concernant les Préparations Pour Nourissons et les Préparations de Suite, Directive de la Commission," Journal officiel des Communautés européennes, 175:35-48 (1991) (French Language).
Commission, "Modifiant la Directive 91/321/CEE Concernant Les Préparations Pour Nourrissons et Les Préparations de Suite," Directive 96/4/CE de la Commission, Journal officiel des Communautés européennes, 49:12-16 (1996) (French Language).
Cosgrove, "Nucleotides," Nutrition, Perinatal and Infant Nutrition, 14(10):748-751 (1998).
Debley et al. "Childhood Asthma Hospitalization Risk After Cesarean Delivery in Former Term and Premature Infants," Annals of Allergy Asthma Immunology, 94:228-233 (2005).
Dunstan et al., "Maternal Fish Oil Supplementation in Pregnancy Reduces Interleukin-13 Levels in Cord Blood of Infants at High risk of Atopy," Clinical & Experimental Allergy, 33:442-448 (2003).
Eggesbo et al., "Is Delivery by Cesarean Section a Risk Factor for Food Allergy?" Journal of Allergy Clinical Immunology, 112(2):420-426 (2003).
Fanaro et al., "Acidic Oligosaccharides from Pectin Hydrolysate as New Component for Infant Formulae: Effect on Intestinal Flora, Stool Characteristics, and pH," Journal of Pediatric Gastroenterology and Nutrition, 41:186-190 (2005).
Fanaro et al., "Intestinal Microflora in Early Infancy: Composition and Development," Acta Paediatrica, Universitetsforlaget, Oslo, Norway, 441:48-55 (2003).
Fanaro et al., "Galacto-Oligosaccharides and Long-Chain Fructo-Oligosaccharides as Prebiotics in Infant Formulas: A Review," Acta Paediatrica Supplement, 94(449):22-26 (2005).
Favier et al., Molecular Monitoring of Succession of Bacterial communities in Human Neonates, Applied and Environmental Microbiology, 68(1):219-226 (2002).
Field et al., "Polyunsaturated Fatty Acids and T-Cell Function: Implications for the Neonate," Lipids, 36(9):1025-1032 (2001).
Fructooligosaccharide, From Wikipedia, http://en.wikipedia.org/wiki/Fructooligosaccharide, pp. 1-4, Jun. 13, 2011.
Fuller, "Probiotics in Human Medicine," GUT, An International Journal of Gastroenterology and Hepatology, 32(4):439-442 (1991).
Gewolb et al., "Stool Microflora in Extremely Low Birthweight Infants," Archives of Disease in Childhood Fetal and Neonatal Edition, 80:F167-F173 (1999).

(56) References Cited

OTHER PUBLICATIONS

Gibson et al., "Dietary Modulation of the Human Colonic Microbiota: Introducing the Concept of Prebiotics," Journal of Nutrition, Critical Review, 125(6):1401-1412 (1995).
Goedhart et al., "The Composition of Human Milk as a Model for the Design of Infant Formulas: Recent Findings and Possible Applications," Nutrition Research Reviews, 7:1-23 (1994).
Grönlund, Minna-Maija, et al., "Fecal Microflora in Healthy Infants Born by Different Methods of Delivery: Permanent Changes in Intestinal Flora After Cesarean Delivery," Journal of Pediatric Gastroenterology and Nutrition, 28(1):19-25 (1999).
Hakansson et al., "Caesarean Section Increases the Risk of Hospital Care in Childhood for Asthma and Gastroenteritis," Clinical & Experimental Allergy, 33:757-764 (2003).
Hall et al., "Factors Influencing the Presence of Faecal Lactobacilli in Early Infancy," Archives of Desease in Childhood, 65(2):185-188 (1990).
Hallstrom et al., "Effects of the Mode of Delivery and Necrotising Enterocolitis on the Intestinal Microflora in Preterm Infants," European Journal of Clinical Microbiology and Infectious Diseases, 23:463-470 (2004).
Heinrich, Negele, et al., "Mode of Delivery and Development of Atopic Disease During the First 2 Years of Life," Pediatric Allergy and Immunology, 15(1):48-54 (2004).
Heyman et al., "Effects of Specific Lactic Acid Bacteria on the Intestinal Permeability to Macromolecules and the Inflammatory Condition," Acta Paediatrica, Universitetsforlaget, Oslo, 94(449):34-36 (2005).
International Search Report for Application No. PCT/NL2006/050246 dated Mar. 19, 2007.
International Search Report for Application No. PCT/NL2009/050364 dated Aug. 18, 2009.
International Search Report in Applciatino No. PCT/NL2006/050248 dated Sep. 4, 2007.
International Search Report in Application No. PCT/EP2006/010159 dated Jan. 30, 2007.
International Search Report in Application No. PCT/NL2006/050247 dated Mar. 1, 2007.
Janas et al, "The Nucleotide Profile of Human Milk," Pediatric Research, 16(8):659-662 (1982).
Journal officiel des Communautes europeenes, N L 175/35, 1991 (French language) Directive of the European Commission of May 14, 1991 Concerning Infant Formulae and Follow-On Formulae.
Kirjavainen et al., "Probiotic Bacteria in the Management of Atopic Disease: Underscoring the Importance of Viability," Journal of Pediatric Gastoenterology and Nutrition, 36:223-227 (2003).
Knol et al., "Colon Microflora in Infants Fed Formula with Galacto- and Fructo-Oligosaccharides: More Like Breast-Fed Infants," Journal of Pediatric Gastroenterology and Nutrition, 40:36-42 (2005).
Koletzko et al., "Polyunsaturated Fatty Acids in Human Milk and Their Role in Early Infant Development," Journal of Mammary Gland Biology and Neoplasia, Plenum Press, New York, NY, 4(3):269-284 (1999).
Kunz et al., "Oligosaccharides in Human Milk: Structural, Functional, and Metabolic Aspects," Annual Review of Nutrition, 20:699-722 (2000).
Laubereau et al., "Caesarean Section and Gastrointestinal Symptoms, Atopic Dermatitis, and Sensitization During the First Year of Life," Archives of Disease in Childhood, 89:993-997 (2007).
Life Start®—Dairy (1.25 oz. powder), Natren, The Probiotic Specialist Recognized Worldwide, 2 pgs., (2006).
Lin et al. "Oral Probiotics Reduce the Incidence and Severity of necrotizing Enterocolitis in Very Low Birth Weight Infants," Pediatrics Official Journal of the American Academy of Pediatrics, 2005, vol. 115, No. 1, pp. 1-4.
Marini et al., "Pro- and pre-biotics administration in preterm infants: colonization and influence on faecal flora," Acta Paediatrica Scandinavica Supplement, 91(441):80-81 (2003) (Abstract Only).
Martin et al., "Isolation of Bifidobacteria From Breast Milk and Assessment of the Bifidobacterial population by PCR-Denaturing Gradient Gel Electrophoresis and Quantitative Real-Time PCR," Applied and Environmental Microbiology, 75(4):965-969 (2009).
Martin et al., "The Commensal Microflora of Human Milk: New Perspectives for Food Bacteriotherapy and Probiotics," Trends in Food Science & Technology, 15(3-4):121-127 (2004).
Martin-Sosa et al., "Sialyloligosaccharides in Human and Bovine Milk and in Infant Formulas: Variations with the Progression of Lactation," Journal of Dairy Science, 86:52-59 (2003).
McVay et al., "Formula Fortified With Live Probiotic Culture Reduces Pulmonary and Gastrointestinal Bacterial Colonization and Translocation in a Newborn Animal Model," Journal of Pediatric Surgery, 43:25-29 (2008).
McVeagh et al., "Human Milk Oligosaccharides: Only the Breast," Journal of Pediatric Child Health, 33(4):281-286 (1997).
Millar et al., "Probiotics for preterm infants," www.archdischild.com, Archives of Disease in Childhood: Fetal & Neonatal, 88(5):F354-F358 (2003).
Morishita et al., Galactooligosaccharide in Combination With Bifidobacterium and Bacteroides Affects the Population of Clostridium Perfringens in the Intestine of Gnotobiotic Mice, Nutrition Research, 22:1333-1341 (2002).
Moro et al., "A Mixture of Prebiotic Oligosaccharides Reduces the Incidence of Atopic Dermatitis During the First Six Months of Age," Archives of Disease in Childhood: Fetal & Neonatal, 91:814-819 (2006).
Moro et al., "Dosage-Related Bifidogenic Effects of Galacto- and Fructooligosaccharides in Formula-Fed Term Infants," Journal of Pediatric Gastroenterology and Nutrition, 34(3):291-295 (2002).
Mullane N.R. et al., "Enterobacter Sakazakii: Biological Properties and Significance in Dried Infant Milk formula (IMF) Powder," International Journal of Dairy Technology, 59(2):102-111 (2006).
Nadkarni et al., Determination of Bacterial Load by Real-Time PCR Using a Broad-Range (Universal) Probe and Primers Set, Microbiology, 148:257-266 (2002).
Neut et al., "Bacterial Colonization of the Large Intestine in Newborns Delivered by Cesarean Section," Zbl Bakt Hyg A, 266:330-337 (1987).
Nutritional Quality of Milkfat reference (accessible at: www.idfdairynutrition.org/Files/media/FactSheetsHP/Final-HP-Factsheet-Milkfat-080125.pdf) (published 2008; last accessed May 5, 2014).
Ouwehand et al., "The Mucus Binding of Bifidobacterium Lactis Bb 12 is Enhanced in the Presence of Lactobacillus GG and Lact. Delbrueckil Subsp. Bugaricus," Applied Microbiology, 30(1):10-13 (2000), Department of Biochemistry and Food Chemistry, University of Turku, Finland.
Rivero, M., "Effect of a New Infant Formulae Enriched Prebiotics, Probiotics, Nucleotides and Lc-Pufa's on Infants Recovery After an Infection," Journal of Pediatric Gastroenterology and Nutrition, 39(1):S482-S483, Jun. 2004.
Satokari et al., "Bifidobacterial Diversity in Human Feces Detected by Genus-Specific PCR and Denaturing Gradient Gel Electrophoresis," Applied and Environmental Microbiology, 67(2):504-513 (2001).
Satorkari et al., "Molecular Approaches for the Detection and Identificationof Bifidobacteria and Lactobacilli in the Human Gastrointestinal Tract," System Applied Microbiology, 26:572-584 (2003).
Scherz et al., "Food Compositions and Nutrition Tables," Medpharm Scientific Publishers Suttgart, 6-7 (1994).
Thillay et al., "Ave Cesar, les bebes qui seront allergiques to detestent!," Arch. Dis. Child, Allergie, France, 89(11):993-997 (2004) (French Language).
Vandenplas, "Oligosaccharides in Infant Formula," British Journal of Nutrition (2002) vol. 87, Suppl. 2, pp. S293-S296.
Varel et al., "Nutritional Features of Baceroides Fragilis Subsp. Fragilis," Applied Microbiology, 18(2):251-257 (1974).
Vidal Dictionary 2001, 32-33 (partial) (see description of Infant Formula Conformil) (French Language).
Vidal Dictionary 2005, 98-99, 111, 112, 121 (see description of Infant Formulas Enfamil Premium on p. 112 and Gallia Calisma on p. 121). (French Language).

(56) References Cited

OTHER PUBLICATIONS

Wikipedia, "Galacto-oligosaccharides", Jun. 28, 2013; http://www.en.wikipedia.org/wiki/galactooligosaccharide, p. 1.
Wikipedia, "Raffinose", Jun. 28, 2013, http://en.wikipedia.org/wiki/raffinose, p. 1.
Willemsen et al., "Specific Poly-Unsaturated Fatty Acids Support Intestinal Barrier Integrity and Reduce I1-4 Mediated Barrier Disruption: PG4-01," Journal of Pediatric Gastroenterology and Nutrition, 40(5):654 (2005).
Xaus et al., "Infant Nutrition as Target," Nutrafoods, 3(2):13-21 (2004).

PREVENTING DISEASES IN INFANTS DELIVERED VIA CAESAREAN SECTION

CROSS-REFERENCE TO RELATED APPLICATION(S)

This application is a Continuation of U.S. application Ser. No. 14/135,171 (now U.S. Pat. No. 9,107,438), filed Dec. 19, 2013, which in turn is a Continuation of U.S. application Ser. No. 12/091,011 (now U.S. Pat. No. 8,715,769), filed as the National Phase of International Patent Application No. PCT/NL2006/050247, filed Oct. 6, 2006, published as WO 2007/046698, which claims priority to European Application No. 05023029.1, filed Oct. 21, 2005. The contents of these applications are herein incorporated by reference in their entirety.

FIELD OF THE INVENTION

The present invention relates to methods for treatment and/or preventing disorders in infants delivered via caesarean section.

BACKGROUND OF THE INVENTION

Human milk contains non-digestible oligosaccharides which specifically stimulate the growth of lactic acid producing bacteria, such as species belonging to the genus *Bifidobacterium* and *Lactobacillus* and prevent the growth and/or adhesion to the intestinal wall of other (pathogenic) bacteria. Hence, when an infant receives human milk, the infant's intestinal flora develops into a healthy flora rich in lactic acid producing bacteria. The presence of a healthy intestinal flora improves gut barrier maturation and/or gut barrier integrity, stimulates the formation of mucus, inhibits pathogenic bacteria and stimulates the immune system.

WO0008984 relates to a mixture of non-digestible carbohydrates for stimulating the health and enhancement of the healthy micro-organisms present in the natural flora of the large intestine.

Before birth the intestinal tract of the infant is normally sterile. During vaginal delivery the intestinal tract of the infant is inoculated with vaginal and/or fecal bacteria of the mother, resulting in a colonization of the infant's gastrointestinal tract by bacteria originating from the infant's environment.

Natren® produces the probiotic product Life Start® which is designed specifically for infants and suitable for infants delivered via caesarean section. Life Start® is made with *Bifidobacterium infantis*. Because the Life Start® product contains only one single *Bifidobacteria* species, the benefits for the infant will be very limited.

SUMMARY OF THE INVENTION

The present inventors have found that infants delivered via caesarean section have an intestinal flora which is different from the intestinal flora of infants born via the vaginal route. Particularly, infants born via caesarean section have a reduced rate of intestinal colonization by *Bifidobacteria* and have a less diverse *Bifidobacterium* intestinal flora regarding species than infants born via the vaginal route, particularly missing *Bifidobacterium breve*, *Bifidobacterium longum*, *Bifidobacterium infantis* and *Bifidobacterium bifidum*.

It was further found that the intestinal flora of infants delivered via caesarean section have a lower content of *Bifidobacteria* compared to the intestinal flora of infants delivered vaginally. Additionally it was found that the intestinal flora of infants born via caesarean section has a high content of (undesirable) *Escherichia coli* 6 weeks after delivery.

The present inventors have found that these deficiencies in the intestinal flora of infants can be overcome by the administration of non-digestible oligosaccharides to the infant born via caesarean section, preferably included in the nutrition of the infant born via caesarean section. Particularly, it was found that the administration of non-digestible oligosaccharides resulted in an increased content of bifidobacteriam in infants delivered via caesarean section, and also reduces *E. coli* content. Overcoming such deficiencies results in improved health and prevents and/or treats a variety of disorders.

A healthy and fully developed gastrointestinal flora has important physiological effects. One important aspect is that it reduces the occurrence of (gastrointestinal) infections. Because infants delivered via a caesarean section lack a healthy flora, preventing infection is particularly important for these infants. These infants are normally delivered in a hospital environment, which is a risk for pathogenic infection due to the occurrence of nosocomial bacteria. Additionally, the impaired development of a healthy intestinal flora results in faster colonization of pathogenic bacteria compared to a situation where the infants intestinal tract is inoculated by maternal bacteria.

The present invention particularly aims to decrease the number and severity of (gastrointestinal) infections in infants born via caesarean section, by (i) stimulating the growth of beneficial bacteria, preferably lactic acid producing bacteria, (ii) decreasing the growth of pathogenic bacteria; and/or (iii) decreasing the adhesion of pathogenic bacteria to the intestinal epithelial cells and/or intestinal mucus.

The present inventors have found that (gastrointestinal) infections can be prevented and treated by non-digestible oligosaccharides, particularly galacto-oligosaccharides. The present non-digestible oligosaccharides are suitable for enteral (particularly oral) administration, making it easy to include these in infant milk formula. The present non-digestible oligosaccharide reduces the occurrence of the infections, as well as reduces the severity of infections due to reduction of intestinal concentrations of pathogens particularly *Staphylococcus aureus*, *Staphylococcus epidermidis*, *Streptococcus haemolyticus*, *Streptococcus*, *Clostridium difficile*, *Bacillus subtilis*, *Pseudomonas aeruginosa*, *Enterobacter*, *Klebsiella*, *Acinetobacter*, *Proteus*, *Aeromonas*, and *Escherichia coli*.

The occurrence and severity of infection in infants delivered via caesarean section can be even further reduced by providing a mixture of at least two non-digestible oligosaccharides differing in structure and/or degree of polymerization (DP), and even further by providing in addition to a non-digestible neutral oligosaccharide an acidic oligosaccharide, particularly uronic acid oligosaccharide. A mixture of non-digestible oligosaccharides differing in structure and/or DP synergistically stimulates the development of a healthy gastrointestinal flora. Galacto-oligosaccharides, and/or fructo-oligosaccharides are particularly suitable as these were found to stimulate the growth of *B. longum*, *B. breve* and/or *B. infantis* (Example 2). Uronic acid oligosaccharides prevent adhesion of pathogenic bacteria to the intestinal wall, thereby further preventing and/or treating infections caused by pathogens.

In addition to a reduced occurrence of infection, other disorders are prevented and/or treated in the infants delivered via caesarean section by the present method. Particularly disorders such as allergy and eczema are prevented and/or treated by stimulating a healthy intestinal flora.

In a further aspect the present invention can be suitably brought to practice by incorporation of the present active ingredients in a nutritional composition. Such composition can be administered to the infant without posing a heavy burden on the infant delivered via caesarean section.

DETAILED DESCRIPTION OF THE PREFERRED EMBODIMENTS

The present method provides the use of a composition comprising non-digestible oligosaccharides for the manufacture of a composition for (i) treatment and/or prevention of disorder in infants delivered via caesarean section and/or (ii) the stimulation of health in infants delivered via caesarean section In a further aspect the present invention provides a method for (i) treatment and/or prevention of disorders in infants delivered via caesarean section and/or (ii) the stimulation of health in infants delivered via caesarean section, said method comprising administering non-digestible oligosaccharide to an infant delivered via caesarean section, preferably a method for the prevention and/or treatment of infection; and/or the prevention and/or treatment of allergy in infants delivered via caesarean section.

In a further aspect the present invention provides a method for stimulating the development of a healthy intestinal flora and/or decreasing the occurrence of intestinal pathogens in an infant born via caesarean section comprising the steps of: a) admixing I) a nutritionally or pharmaceutically acceptable liquid; and II) a dry composition, wherein the dry composition II comprises non-digestible oligosaccharide and b) administering the composition obtained in step a) to the infant.

In still a further aspect the present invention provides a method for stimulating the development of a healthy intestinal flora and/or decreasing intestinal pathogens in an infant delivered via caesarean section, comprising administering to the infant a composition comprising a non-digestible oligosaccharide.

In a further aspect the present invention provides a method for providing nutrition to an infant delivered via caesarean section, said method comprising the steps of: a) admixing a composition comprising non-digestible oligosaccharide with a nutrition to be administered to the infant delivered via caesarean section; and b) administering the mixture obtained in step a) to the infant delivered via caesarean section. The invention also relates to a composition comprising at least 5 wt. % non-digestible oligosaccharide based on dry weight of the composition and at least 1 wt. % uronic acid oligosaccharide based on dry weight of the composition.

Caesarean Section

The present invention relates to the enteral administration of a composition comprising non-digestible oligosaccharides to infants delivered via caesarean section. A caesarean section (c-section) is a surgical procedure where an infant is delivered through an incision made in the mother's abdominal wall, and then through the wall of the uterus. A caesarean section is usually performed when it is safer for the mother or the infant than a vaginal delivery. Alternatively, a woman may choose to have a caesarean section rather than deliver her infant vaginally.

Non-Digestible Oligosaccharides

The present composition comprises a non-digestible oligosaccharide, which preferably stimulates the growth of the intestinal lactic acid producing bacteria, particularly *Bifidobacteria* and/or the *Lactobacilli*.

The term "oligosaccharide" as used in the present invention refers to saccharides with a degree of polymerization (DP) of 2 to 250, preferably a DP 2 to 100, more preferably 2 to 60, even more preferably 2 to 10. If the oligosaccharide with a DP of 2 to 100 is included in the present composition, this includes compositions which contain oligosaccharides with a DP between 2 and 5, a DP between 50 and 70 and a DP of 7 to 60. The term "non-digestible oligosaccharide" as used in the present invention refers to oligosaccharides which are not or only partially digested in the intestine by the action of acids or digestive enzymes present in the human upper digestive tract (small intestine and stomach) but which are fermented by the human intestinal flora. For example, sucrose, lactose, maltose and maltodextrins are considered digestible. Preferably the non-digestible oligosaccharide is a non-digestible neutral oligosaccharide. The term "neutral oligosaccharide" as used in the present invention refers to oligosaccharides wherein more than 75% of the saccharides units are selected from the group consisting of glucose, fructose, galactose, mannose, ribose, rhamnose, arabinose, and xylose, preferably more than 85%, more preferably more than 95%, even more preferably more than 99%. Preferred neutral oligosaccharides are transgalacto-oligosacharides and fructo-oligosaccharides.

Preferably the present non-digestible oligosaccharide is a prebiotic oligosaccharide. The term "prebiotic oligosaccharide" refers to a non-digestible oligosaccharide that beneficially affects the host by selectively stimulating the growth and/or activity of one or a limited number of probiotic bacterial species in the colon.

Preferably the present non-digestible oligosaccharide is soluble. The term "soluble" as used herein, when having reference to a polysaccharide, fiber or oligosaccharide, means that the substance is at least soluble according to the method described by L. Prosky et al., J. Assoc. Off. Anal. Chem. 71, 1017-1023 (1988).

Preferably the present composition comprises at least one non-digestible oligosaccharide selected from the group consisting of galacto-oligosaccharides, non-digestible dextrins, xylo-oligosaccharides, arabino-oligosaccharides, gluco-oligosaccharides (including gentio-oligosaccharides and cyclodextrins), chito-oligosaccharides, fuco-oligosaccharides, manno-oligosaccharides, isomalto-oligosaccharides fructo-oligosaccharides (including inulin), galactomanno-oligosaccharides, glucomanno-oligosaccharides, and arabinogalacto-oligosaccharides; more preferably at least galacto-oligosaccharides and/or fructo-oligosaccharides, most preferably at least galacto-oligosaccharides.

The term "fructo-oligosaccharide" as used herein refers to a non-digestible polysaccharide carbohydrate comprising a chain of at least 2 β-linked fructose units, with a DP of 2 to 250, preferably 7 to 100, more preferably 20 to 60. Preferably inulin is used. Inulin is available under the tradename "Raftilin HP®", (Orafti). The average DP of the present fructo-oligosaccharide is preferably at least 7, more preferably at least 10, preferably below 100. The fructo-oligosaccharide used preferably has the (majority of) fructose units linked with a β(2→1) linkage. Other terms for fructooligosaccharides include inulin, fructopolysaccharide, polyfructose, fructans and oligofructose. The present composition preferably comprises fructo-oligosaccharides with a DP of 2 to 100.

Non-digestible dextrins refer to digestion-resistant (malto)dextrins or digestion-resistant polydextrose which preferably have a DP of 10 to 50, preferably between 10 and 20. The non-digestible dextrins preferably comprise α(1→4), α(1→6) glucosidic bonds and 1→2 and 1→3 linkages Non-digestible dextrins are for example available under the tradename "Fibersol 2®" from Matsutami Industries or Litesse® from Danisco.

The present inventors found that galacto-oligosaccharides can be advantageously used in the present composition, because these oligosaccharides where particularly effective in stimulating the growth of *Bifidobacteria*. Hence, in a preferred embodiment the present composition comprises galacto-oligosaccharides. The term "galacto-oligosaccharide" as used herein refers to a non-digestible oligosaccharide, wherein at least 30% of the saccharide units are galactose units, preferably at least 50%, more preferably at least 60%. The present composition preferably comprises galacto-oligosaccharides with a DP of 2-100, more preferably a DP of 2-10. Preferably the saccharides of the galacto-oligosaccharide are β-linked, as is the case in human milk oligosaccharides.

Preferably the present composition comprises a galacto-oligosaccharide selected from the group consisting of trans-galacto-oligosaccharides, lacto-N-tetraose (LNT) and lacto-N-neotetraose (neo-LNT). In a particularly preferred embodiment the present method comprises the administration of transgalacto-oligosaccharide ([galactose]$_n$-glucose; wherein n is an integer between 1 and 60, i.e. 2, 3, 4, 5, 6, . . . , 59, 60; preferably n is 2, 3, 4, 5, 6, 7, 8, 9 and/or 10). Transgalacto-oligosaccharides (TOS) are for example sold under the trademark Vivinal™ (Borculo Domo Ingredients, Netherlands).

The present composition preferably comprises 0.5 to 75 grams of the non-digestible oligosaccharides per 100 gram dry weight, preferably between 0.5 and 50 grams. The present composition preferably comprises 0.1 to 75 grams of the galacto-oligosaccharides per 100 gram dry weight, preferably between 0.1 and 50 grams.

The present method preferably comprises the administration of a serving comprising between 0.05 and 25 grams non-digestible oligosaccharide, preferably between 0.1 and 5 grams. The present method preferably comprises the administration of a serving comprising between 0.05 and 25 grams galacto-oligosaccharides, preferably between 0.1 and 5 gram galacto-oligosaccharides.

The present inventors have also found that a mixture of a long chain non-digestible (neutral) oligosaccharides and short chain non-digestible (neutral) oligosaccharides synergistically stimulate the growth of a healthy intestinal flora, particularly *Bifidobacteria* and reduces the occurrence of *E. coli* in infants delivered via caesarean section.

The present composition thus preferably comprises at least two non-digestible (neutral) oligosaccharides with different average degrees of polymerization (DP). Preferably the weight ratios:

a. (non-digestible (neutral) oligosaccharides with DP 2 to 5):(non-digestible (neutral) oligosaccharides with DP 6, 7, 8, and/or 9)>1; and/or
b. (non-digestible (neutral) oligosaccharides with DP 10 to 60):(non-digestible (neutral) oligosaccharides with DP 6, 7, 8, and/or 9)>1 Preferably both weight ratios are above 2, even more preferably above 5.

For further improvement, the present non-digestible oligosaccharide preferably has a relatively high content of short chain oligosaccharides, as these strongly stimulate the growth of *Bifidobacteria*. Hence, preferably at least 10 wt. % of the non-digestible oligosaccharides in the present composition has a DP of 2 to 5 (i.e. 2, 3, 4, and/or 5) and at least 5 wt. % has a DP of 10 to 60. Preferably at least 50 wt. %, more preferably at least 75 wt. % of the non-digestible neutral oligosaccharides have a DP of 2 to 9 (i.e. 2, 3, 4, 5, 6, 7, 8, and/or 9).

To improve the biodiversity and stimulate the growth of multiple intestinal organisms, the present composition preferably comprises two non-digestible oligosaccharides with a different structure. The present composition preferably comprises at least two different non-digestible (neutral) oligosaccharides, wherein the oligosaccharides have a homology in saccharide units below about 90%, preferably below 50%, even more preferably below 25%, even more preferably below 5%. The term "homology" as used in the present invention is the cumulative of the percentage of same saccharide unit in the different oligosaccharides. For example, oligosaccharide 1 (OL1) has the structure fruc-fruc-glu-gal, and thus comprises 50% fruc (fructose), 25% gal (galactose) and 25% glu (glucose). Oligosaccharide 2 (OL2) has the structure fruc-fruc-glu, and thus comprises 66% fruc, 33% glu. The different oligosaccharides thus have a homology of 75% (50% fruc+25% glu).

The present composition preferably comprises galacto-oligosaccharides and fructo-oligosaccharides, more preferably transgalacto-oligosacharides with a DP of 2-7 and fructo-oligosaccharides with a DP of 10-100.

Uronic Acid Oligosaccharides

The present composition preferably comprises uronic acid oligosaccharides, more preferably a combination of non-digestible neutral oligosaccharide and uronic acid oligosaccharide. The uronic acid oligosaccharide (further) reduces the adherence of pathogens to the intestinal epithelia and suppresses colonization by intestinal pathogens.

The term uronic acid oligosaccharide as used in the present invention refers to an oligosaccharide wherein preferably at least 25%, preferably at least 50% of the monosaccharide units present in the oligosaccharide is one selected from the group consisting of guluronic acid, mannuronic acid, iduronic acid, riburonic acid, galacturonic acid and glucuronic acid. In a preferred embodiment the uronic acid oligosaccharide comprises at least 50% galacturonic acid based on total uronic acid units in the uronic acid oligosaccharide. The uronic acid oligosaccharides used in the invention are preferably prepared from pectin, pectate, alginate, chondroitine, hyaluronic acids, heparine, heparane, bacterial carbohydrates, sialoglycans, fucoidan, fuco-oligosaccharides and/or carrageenan, more preferably from pectin and/or alginate, even more preferably from pectin, most preferably polygalacturonic acid. The present uronic acid oligosaccharide is preferably a pectin degradation product and/or alginate degradation product. Preferably the pectin degradation product is a pectin hydrolysate (prepared by hydrolysis) and/or pectin lysate (prepared by beta-elimination). The pectin degradation product is preferably prepared from fruit and/or vegetable pectin, more preferably apple pectin, citrus pectin and/or sugar beet pectin, more preferably from apple, citrus and/or sugar beet pectin. The pectin degradation product is preferably prepared with lyases and/or variations of the temperature and pressure, more preferably with pectin lysate, i.e. by beta-elimination. The pectin degradation product is preferably a pectin lysate Preferably the present composition comprises uronic acid oligosaccharide with a DP of 2 to 250, more preferably a DP of 2 to 100, even more preferably a DP of 2 to 50, most preferably a DP of 2 to 20. Preferably the present composition comprises between 25 and 100 wt. %, more preferably between 50 and 100 wt. % uronic acid oligosaccharide with a DP of 2 to 250 based on total weight of uronic acid in the composition, more preferably a DP of 2 to 100, even more preferably a DP of 2 to 50, most preferably a DP of 2 to 20.

The present uronic acid oligosaccharide is preferably obtainable by enzymatic digestion of pectin with pectin lyases, pectic lyase, endopolygalacturonase and/or pectinase.

In a preferred embodiment at least one of the terminal hexuronic acid units of the uronic acid oligosaccharide has a double bond, which is preferably situated between the $C_4$ and $C_5$ position of the terminal hexuronic acid unit. The double bond effectively protects against attachment of the pathogenic bacteria to the intestinal epithelial cells. Preferably one of the terminal hexuronic acid units comprises the double bond. The double bond at terminal hexuronic acid unit can for example be obtained by enzymatic hydrolysis of pectin with lyase.

In a further embodiment, a mixture of uronic acid oligosaccharides is used, which have a different DP and/or comprise both unsaturated and saturated terminal hexuronic acid units. Preferably at least 5%, more preferably at least 10%, even more preferably at least 25% of the terminal hexuronic acid units of the uronic acid oligosaccharide is an unsaturated hexuronic acid unit. As each individual uronic acid oligosaccharide preferably comprises only one unsaturated terminal hexuronic acid unit, preferably less than 50% of the terminal hexuronic acid units is an unsaturated hexuronic acid unit (i.e. comprises a double bond). A mixture of uronic acid oligosaccharides preferably contains between 2 and 50% unsaturated terminal hexuronic acid units based on the total amount of terminal hexuronic acid units, preferably between 10 and 40%.

The uronic acid oligosaccharide can be derivatized. The uronic acid oligosaccharide may be methoxylated and/or amidated. In one preferred embodiment the uronic acid oligosaccharides are characterized by a degree of methoxylation above 20%, preferably above 30% even more preferably above 70%. As used herein, "degree of methoxylation" (also referred to as DE or "degree of esterification") is intended to mean the extent to which free carboxylic acid groups contained in the uronic acid oligosaccharide have been esterified (e.g. by methylation). In another preferred embodiment the uronic acid oligosaccharides have a degree of methylation above 20%, preferably above 30%, even more preferably above 70%.

The present composition preferably comprises between 0.01 and 10 grams uronic acid oligosaccharide with a DP of 2 to 250 per 100 gram dry weight of the present composition, more preferably between 0.05 and 6 gram, even more preferably 0.2 to 2 gram per 100 gram dry weight. The present composition preferably comprises between 0.01 and 10 grams galacturonic acid oligosaccharide with a DP of 2 to 250 (more preferably a DP of 2 to 100) per 100 gram dry weight of the present composition, more preferably between 0.05 and 6 gram, even more preferably 0.2 to 2 gram.

The uronic acid oligosaccharides are preferably non-digestible in the upper human intestinal tract and water-soluble (according to the method disclosed in L. Prosky et al, J. Assoc. Anal. Chem 71: 1017-1023, 1988). The uronic acid oligosaccharides are preferably fermentable by the intestinal flora. The uronic acid oligosaccharides of the invention advantageously reduce the adhesion of pathogenic micro-organisms to the intestinal epithelial cells, thereby reducing colonization of (nosocomial) pathogenic bacteria in the colon of the infant delivered by caesarean section. Furthermore, the uronic acid oligosaccharides of the present invention preferably stimulate the formation of a healthy intestinal flora and are fermented, resulting in a production of intestinal organic acids and a reduction of intestinal pH, which inhibit the growth of (nosocomial) pathogenic bacteria.

Lactic Acid Producing Bacteria

The present composition preferably comprises lactic acid producing bacteria, either living or dead. Lactic acid producing bacteria are preferably provided as a mono- or mixed culture of live microorganisms. The present composition preferably comprises $10^2$ to $10^{13}$ colony forming units (cfu) of lactic acid producing bacteria per gram dry weight of the present composition, preferably $10^2$ to $10^{12}$, more preferably $10^5$ to $10^{10}$, most preferably from $10^4$ to $5\times10^9$ cfu.

Preferably the present composition comprises bacteria of the genus *Lactobacillus* or *Bifidobacterium*. Preferably the composition comprises at least one *Bifidobacterium* selected from the group consisting of *B. longum, B. breve, B. infantis, B. catenulatum, B. pseudocatenulatum, B. adolescentis, B. animalis, B. gallicum, B. lactis* and *B. bifidum*, more preferably *B. breve, B. infantis, B. bifidum, B. catenulatum, B. longum*, more preferably *B. longum* and *B. breve*, most preferably *B. breve*. Preferably the composition comprises at least two different *Bifidobacterium* species, subspecies or strains. The present composition preferably comprises at least one, more preferably at least two, even more preferably at least three, most preferably at least four different *Bifidobacterium* species. The present composition preferably comprises at least one, more preferably at least two, even more preferably at least three, most preferably at least four different *Bifidobacterium* strains. Preferably the present composition comprises at least *B. longum* and *B. breve*. The above-mentioned combinations commonly aim to increase the diversity and/or the quantity of microorganisms in the intestine of the caesarean section delivered infant. This beneficially affects the infant, proving numerous health benefits.

Preferably the present composition comprises a *Lactobacillus* selected from the group consisting of *L. casei, L. reuteri, L paracasei, L. rhamnosus, L. acidophilus, L. johnsonii, L. lactis, L. salivarius, L. crispatus, L. gasseri, L. zeae, L. fermentum* and *L. plantarum*, more preferably *L. casei, L. paracasei, L. rhamnosus, L. johnsonii, L. acidophilus, L. fermentum* and most preferably *L. paracasei*. Even more preferably the present composition comprises *Bifidobacterium breve* and/or *Lactobacillus paracasei*, because the growth of these bacteria in impaired in the intestine of formula fed infants compared to breast fed infants. The further increased biodiversity will have a stimulatory effect on health of the newborn delivered by caesarean section.

Long-Chain Polyunsaturated Fatty Acids

The present composition preferably comprises long chain polyunsaturated fatty acids (LC-PUFA). LC-PUFA are fatty acids or fatty acyl chains with a length of 20 to 24 carbon atoms, preferably 20 or 22 carbon atoms comprising two or more unsaturated bonds. More preferably the present composition comprises eicosapentaenoic acid (EPA, n-3), docosahexaenoic acid (DHA, n-3) and/or arachidonic acid (ARA, n-6). These LC-PUFA effectively reduce intestinal tight junction permeability. Reduced tight junction permeability reduced the occurrence of infection and/or reduces passage of allergens. Hence incorporation of EPA, DHA and/or ARA in the present composition improves intestinal barrier integrity, which is of utmost important for babies delivered via a caesarean section since these babies have a less developed intestinal flora and hence a slower maturing gut barrier. The incorporation of these LC-PUFA's will further contribute (synergistically) to the reduced occurrence and severity of infections and allergy.

Since low concentration of ARA, DHA and/or EPA are already effective in reducing tight junction permeability, the content of LC-PUFA with 20 and 22 carbon atoms in the present composition preferably does not exceed 15 wt. % of the total fat content, preferably does not exceed 10 wt. %, even more preferably does not exceed 5 wt. % of the total fat content. Preferably the present composition comprises at least 0.1 wt. %, preferably at least 0.25 wt. %, more preferably at least 0.6 wt. %, even more preferably at least 0.75 wt. % LC-PUFA with 20 and 22 carbon atoms based on total fat content. For the same reason, the EPA content preferably does not exceed 5 wt. % of the total fat, more preferably does not exceed 1 wt. %, but is preferably at least 0.03 wt. %, more preferably at least 0.05 wt. % of the total fat. The DHA content preferably does not exceed 5 wt. %, more preferably does not exceed 1 wt. %, but is at least 0.1 wt. % of the total fat. As ARA was found to be particularly effective in reducing tight junction permeability, the present composition comprises relatively high amounts, preferably at least 0.1 wt. %, even more preferably at least 0.25 wt. %, most preferably at least 0.35 wt. % of the total fat. The ARA content preferably does not exceed 5 wt. %, more preferably does not exceed 1 wt. % of the total fat. When the present enteral composition comprises EPA and DHA are advantageously added to balance the action of ARA, e.g. reduce the potential pro-inflammatory action of ARA metabolites. Excess metabolites from ARA may cause inflammation. Hence, the present composition preferably comprises ARA, EPA and DHA, wherein the weight ratio ARA/DHA preferably is above 0.25, preferably above 0.5, even more preferably above 1. The ratio is preferably below 25, more preferably below 15. The weight ratio ARA/EPA is preferably between 1 and 100, more preferably between 5 and 20.

The present composition preferably comprises between 5 and 75 wt. % polyunsaturated fatty acids based on total fat, preferably between 10 and 50 wt. %.

The content of LC-PUFA, particularly the LC-PUFA with 20 and 22 carbon atoms, preferably does not exceed 3 wt. % of the total fat content as it is desirable to mimic human milk as closely as possible. The LC-PUFA may be provided as free fatty acids, in triglyceride form, in diglyceride form, in monoglyceride form, in phospholipid form, or as a mixture of one of more of the above. The present composition preferably comprises at least one of ARA and DHA in phospholipid form.

Nucleotides

Preferably the present composition comprises nucleotides and/or nucleosides, more preferably nucleotides. Preferably, the composition comprises cytidine 5'-monophospate, uridine 5'-monophospate, adenosine 5'-monophospate, guanosine 5'-monophospate, and/or inosine 5'-monophospate, more preferably cytidine 5'-monophospate, uridine 5'-monophospate, adenosine 5'-monophospate, guanosine 5'-monophospate, and inosine 5'-monophospate.

Preferably the composition comprises 5 to 100, more preferably 5 to 50 mg, most preferably 10 to 50 mg nucleotides and/or nucleosides per 100 gram dry weight of the composition. The presence of nucleotides and/or nucleotides advantageously enhances gut growth and maturation in the infant, which is of crucial importance in infants delivered by caesarean section. The nucleotides and/or nucleosides further stimulate the immune system thereby enhancing protection against a high load of intestinal pathogens such as *E. coli*. The nucleotides and/or nucleosides are deemed to act synergistically with the other ingredients of the present composition.

Formulae

The present composition is preferably enterally administered, more preferably orally.

The present composition is preferably a nutritional formula, preferably an infant formula. The present composition can be advantageously applied as a complete nutrition for infants. The present composition preferably comprises a lipid component, protein component and carbohydrate component and is preferably administered in liquid form. The present invention includes dry food (e.g. powders) which are accompanied with instructions as to admix said dry food mixture with a suitable liquid (e.g. water).

The present invention advantageously provides to a composition wherein the lipid component provides 5 to 50% of the total calories, the protein component provides 5 to 50% of the total calories, and the carbohydrate component provides 15 to 90% of the total calories. Preferably, in the present composition the lipid component provides 35 to 50% of the total calories, the protein component provides 7.5 to 12.5% of the total calories, and the carbohydrate component provides 40 to 55% of the total calories. For calculation of the % of total calories for the protein component, the total of energy provided by the proteins, peptides and amino acids needs to be taken into account.

The present composition preferably comprises at least one lipid selected from the group consisting of animal lipid (excluding human lipids) and vegetable lipids. Preferably the present composition comprises a combination of vegetable lipids and at least one oil selected from the group consisting of fish oil, animal oil, algae oil, fungal oil, and bacterial oil. The present composition comprising non-digestible oligosaccharides excludes human milk.

The protein component used in the nutritional preparation are preferably selected from the group consisting of non-human animal proteins (preferably milk proteins), vegetable proteins (preferably soy protein and/or rice protein), free amino acids and mixtures thereof. Cow's milk derived nitrogen source. The present composition preferably contains casein, whey, hydrolysed casein and/or hydrolysed whey protein. Preferably the protein comprises intact proteins, more preferably intact bovine whey proteins and/or intact bovine casein proteins. As the present composition is suitably used to reduce the allergic reaction in an infant, the protein of is preferably selected from the group consisting of hydrolyzed milk protein. Preferably the present composition comprises hydrolyzed casein and/or hydrolyzed whey protein, vegetable protein and/or amino acids. The use of these proteins further reduced the allergic reactions of the infant. The use of these hydrolysed proteins advantageously improves the absorption of the dietary protein component by the immature intestine of the infant delivered by caesarean section.

The present composition preferably contains digestible carbohydrates selected from the group consisting of sucrose, lactose, glucose, fructose, corn syrup solids, starch and maltodextrins, more preferably lactose.

Stool irregularities (e.g. hard stools, insufficient stool volume, diarrhea) is an important problem in babies delivered via caesarean section. This may be caused by the high content of *E. coli* in the feces. It was found that stool problems may be reduced by administering the present non-digestible oligosaccharides in liquid food with an osmolality between 50 and 500 mOsm/kg, more preferably between 100 and 400 mOsm/kg. The reduced stool irregularities enhance the colonization and development of a healthy intestinal flora.

In view of the above, it is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml, most preferably between 0.6 and 0.8 kcal/ml.

Concentrated Non-digestible Oligosaccharides

According to a further preferred embodiment, the present inventions provides a method for providing nutrition to an infant delivered via caesarean section, wherein a composition containing oligosaccharides, preferably a concentrated compositions containing high amounts of oligosaccharides, is admixed to the nutrition to be administered o the infant born via caesarean section. Providing a concentrated form enables the addition of the present non-digestible oligosaccharides to both synthetic infant milk formula but also breast milk.

The present invention thus provides a method for providing nutrition to an infant delivered via caesarean section, said method comprising the steps of:

a) admixing a composition comprising non-digestible oligosaccharide with a nutrition to be administered to the infant delivered via caesarean section; and
b) administering the mixture obtained in step a) to the infant delivered via caesarean section.

Preferably the nutrition as referred to in step a) of the method is infant milk formula or human breast milk. The composition comprising non-digestible oligosaccharides as used in step a) is a concentrated composition of non-digestible oligosaccharides or in other words is a composition comprising non-digestible oligosaccharides in high amounts.

The composition comprising non-digestible oligosaccharide as used in step a) in the above-described method, preferably comprises at least 5 wt. %, preferably at least 10 wt. %, more preferably at least 25 wt. % non-digestible oligosaccharide based on dry weight of the composition, wherein the non-digestible oligosaccharide is preferably selected from the group consisting of galacto-oligosaccharides, non-digestible dextrins, xylo-oligosaccharides, arabino-oligosaccharides, gluco-oligosaccharides (including gentio-oligosaccharides and cyclodextrins), chito-oligosaccharides, fuco-oligosaccharides, manno-oligosaccharides, isomalto-oligosaccharide and fructo-oligosaccharide (including inulins). This composition can be improved by combining it with one or more of the components as disclosed above, preferably one or more or all selected from the group of uronic acid oligosaccharides, LC-PUFA, nucleotides and probiotic bacteria.

The present invention also provides a composition which can be suitably used in the present method for admixing to a nutrition, i.e. a composition which comprises a high concentrations of non-digestible neutral oligosaccharide. The composition comprises at least 5 wt. % (preferably at least 10 wt. %) non-digestible oligosaccharide based on dry weight of the composition, wherein the non-digestible oligosaccharide is preferably selected from the group consisting of galacto-oligosaccharides, non-digestible dextrins, xylo-oligosaccharides, arabino-oligosaccharides, gluco-oligosaccharides (including gentio-oligosaccharides and cyclodextrins), chito-oligosaccharides, fuco-oligosaccharides, manno-oligosaccharides, isomalto-oligosaccharide and fructo-oligosaccharide (including inulins); and at least 1 wt. % (preferably at least 10 wt. %) of an uronic acid oligosaccharide, preferably as defined above, based on dry weight of the composition. The composition preferably contain galactooligosaccharides and/or fructooligosaccharides.

The composition is preferably designed to be added to a single serving of infant nutrition. The cumulative weight of the non-digestible oligosaccharide in the present composition is preferably between 0.1 and 10 gram, preferably between 0.2 and 5 gram per serving. The composition is preferably packed per serving, i.e. in a unit dose of one serving, preferably in the form of a sachet. On serving of the composition preferably has a dry weight of 0.5 to 25 grams, preferably between 1 and 10 grams.

Application

The present invention provides (i) the treatment and/or prevention of a disorder in infants delivered via caesarean section and/or (ii) the stimulation of health in infants delivered via caesarean section. The disorder is preferably selected from the group consisting of intestinal disorders caused by low bifidogenic flora. Preferably the disorder is selected from the group of infection and allergy. The present invention preferably provides a method for the prevention and/or treatment of infections and/or infection disorders, particularly gastrointestinal infections, more preferably the treatment and/or prevention of infections caused by one or more micro-organisms selected from the group consisting of *Staphylococcus* (especially *S. aureus, S. epidermidis, S. haemolyticus*), *Streptococcus* (especially *Streptococcus* group B), *Clostridium* (especially *C. difficile*), *Bacillus* (especially *B. subtilis*, *Pseudomonas* (especially *P. aeruginosa*), *Enterobacter, Klebsiella, Acinetobacter, Proteus, Aeromonas*, and *Escherichia coli*, preferably *Escherichia coli* (*E. coli*). Preferably, the present composition is used in a method for treatment and/or prevention of intestinal infection, urinary tract infection, intestinal inflammation and/or diarrhea in infants delivered by caesarean section. Preferably the present composition is used in a method for modulating the immune system in infants born via caesarean section. Preferably the present composition is used in a method modulate the immune system, preferably resulting in the protection of the infant from allergy.

The present composition is preferably administered to the infant delivered via caesarean section in the first year of life, preferably within 3 months after birth, even more preferably within two weeks after birth, even more preferably within 100 hours, more preferably within 72 hours, most preferably within 48 hours after birth.

The present invention also provides a method for stimulating the development of a healthy intestinal flora in an infant comprising step A: admixing I) a nutritionally or pharmaceutically acceptable liquid; and II) a dry composition, wherein the dry composition II comprises non-digestible oligosaccharides; and step B) administering the composition obtained in step A to an infant born via caesarean section.

Administration of the present composition results in an improved intestinal flora and/or in the formation of organic acids as metabolic end products of microbial fermentation. An increased amount of organic acids results in an increased mucus production, improves gut maturation and/or and increased gut barrier. Hence, in a further aspect, the present invention provides a method for treatment and/or prevention of allergy (particularly food allergy), atopic eczema (e.g. atopic dermatitis), asthma, allergic rhinitis, allergic conjunctivitis in infants delivered by caesarean section, said method comprising administering to the infant a composition comprising the present non-digestible (neutral) oligosaccharides.

Furthermore, administration of the present composition strengthens the immune system. In a further aspect, the present invention therefore provides a method for treatment and/or prevention of systemic infections, otitis and/or respiratory infections in infants delivered by caesarean section.

EXAMPLES

Example 1

Molecular Characterization of Intestinal Microbiota in Infants Born by Vaginal Delivery Vs. Caesarean Delivery In the present study the influence of mode of delivery (caesarean delivery versus vaginal delivery) on the intestinal microbial composition at the third day of life by was studied using by PCR amplification with species-specific primers for ten *Bifidobacterium* species, three *Ruminococcus* species and one *Bacteroides* species.

The microbial DNA was extracted and analyzed according to Favier et al, Environ Microbiol 2002; 68:219-226 and Satokari et al, Appl Environ Microbiol 2001; 67:504-513; Satorkari et al System Appl Microbiol 2003; 26:572-584.

The results of the *Bifidobacterium* and other species detected in faecal samples of 21 newborns after caesarean delivery obtained at the 3rd day of life are given in Table 1. Table 2 gives the *Bifidobacterium* and other species detected in faecal samples of 21 newborns after vaginal delivery obtained at the 3rd day of life. No signal specific for the species *B. dentium, B. angulatum, B. lactis, Ruminococcus bromii, Ruminococcus callidus* and *Ruminococcus obeum* was observed in the faeces of infants delivered by caesarean section as well as of vaginally delivered infants.

It can be concluded that the microbial flora of an infant born via caesarean section differs from that of an infant born via the vaginal route. Not only is the amount of bifidobacteria and other species quantitatively much lower, also on a species level the flora of caesarean section delivered infants is less diverse. Since *Bifidobacterium* is the dominant genus in infant's flora these results can also be generalised to less intestinal bacteria and a less diverse intestinal flora in caesarean section delivered infants, leaving the intestine more susceptible to colonisation by (nosocomial) pathogens.

These results are indicative for the advantageous use of the composition and method according to the present invention, e.g. a method for feeding babies born via caesarean section, decreasing intestinal pathogens, stimulating a healthy intestinal flora and consequently preventing infection, stimulating a healthy immune system, and stimulating gut maturation.

TABLE 1

| | Caesarean section delivered infants | | | | | | | |
|---|---|---|---|---|---|---|---|---|
| NEWBORN | *B. breve* | *B. infantis* | *B. bifidum* | *B. catenulatum* group | *B. adolescentis* | *B. longum* | *B. gallicum* | *Bacteroides fragilis* |
| 1 | − | − | − | − | − | − | − | − |
| 2 | − | − | − | − | − | ++ | − | − |
| 3 | − | − | − | − | − | − | − | − |
| 4 | − | − | − | − | − | − | − | − |
| 5 | − | − | − | − | − | − | − | − |
| 6 | − | − | − | − | − | − | − | − |
| 7 | − | − | − | − | − | − | − | − |
| 8 | − | − | − | − | − | − | − | − |
| 9 | − | − | − | − | − | − | − | − |
| 10 | − | − | − | − | − | − | ++ | − |
| 11 | − | − | − | − | − | − | − | − |
| 12 | − | − | − | − | − | − | − | − |
| 13 | − | − | − | − | − | − | − | − |
| 16 | − | − | − | − | − | − | − | − |
| 17 | − | − | − | − | − | − | − | − |
| 18 | − | − | − | − | − | − | − | − |
| 19 | − | − | − | − | − | − | − | − |
| 20 | − | − | − | − | − | − | − | − |
| 21 | − | − | − | − | − | − | − | − |
| 22 | − | − | − | − | − | − | − | − |
| 23 | − | − | − | − | − | − | − | − |

− = no amplification;
+/− = weak amplification;
+ = positive amplification;
++ = strong amplification

TABLE 2

Vaginally delivered infants

| NEWBORN | B. breve | B. infantis | B. bifidum | B. catenulatum group | B. adolescentis | B. longum | B. gallicum | Bacteroides fragilis |
|---|---|---|---|---|---|---|---|---|
| 1a | − | + | − | − | − | ++ | − | − |
| 2a | +/− | − | ++ | ++ | − | ++ | − | − |
| 3a | − | − | − | + | − | − | − | − |
| 4a | +/− | − | − | ++ | + | + | − | − |
| 5a | +/− | − | ++ | ++ | − | ++ | ++ | − |
| 6a | − | − | +/− | ++ | − | ++ | − | − |
| 7a | − | − | +/− | ++ | ++ | − | − | − |
| 8a | ++ | ++ | − | + | ++ | − | − | − |
| 9a | − | − | − | + | ++ | + | − | − |
| 10a | ++ | − | − | + | + | − | − | − |
| 11a | ++ | − | ++ | ++ | − | ++ | − | + |
| 12a | + | + | + | + | − | ++ | − | + |
| 13a | +/− | − | − | + | − | + | − | − |
| 16a | − | − | − | ++ | − | + | − | − |
| 17a | +/− | − | + | + | − | + | − | − |
| 18a | +/− | − | + | + | − | + | − | − |
| 19a | + | − | − | + | − | + | − | − |
| 20a | − | − | − | + | − | + | − | − |
| 21a | − | − | − | + | ++ | + | − | − |
| 22a | − | + | − | ++ | − | + | − | − |
| 23a | + | − | ++ | ++ | − | + | − | − |

− = no amplification;
+/− = weak amplification;
+ = positive amplification;
++ = strong amplification

Example 2

Effect of Non-Digestible Oligosaccharides on the Flora in Caesarean Delivered Infants Infants were administered infant formula supplemented with 0.8 g/100 ml galacto-oligosaccharides (GOS) with an average DP between 2 and 7 and fructo-oligosaccharides with (FOS, Raftilin HP®) (GFSF-group) or standard infant formula without non-digestible oligosaccharides (SF-group).

The bifidobacterial content in the feces was determined. The percentage of the genus *Bifidobacterium* as a percentage of total bacteria in the first week was 4.3% in caesarean delivered infants (n=44) versus 19.8% in vaginally delivered infants (n=28). At 6 weeks the percentage bifidobacteria was 12.3% in the SF-group of caesarean delivered infants (n=21) and 17.2% in the GFSF-group of the caesarean infants (n=13). The fecal pH of the SF-group of caesarean delivered infants was 7.2 versus 6.5 of the GFSF-group of caesarean delivered infants. The percentage *E. coli* was 11.8% in the SF group of caesarean delivered infants and 0% in the GFSF-group of the caesarean delivered infants. (see Table 3)

These results indicate that administration of non-digestible neutral oligosaccharides to infants born via caesarean section (GFSF group) results in a more bifidogenic flora and a reduced content of potentially pathogenic bacteria compared to infants born via caesarean section that do not receive non-digestible oligosaccharides (the SF group). Additionally the results indicate a reduced content of *E. coli* due to the administration of non-digestible oligosaccharides. The results are indicative for the advantageous use of non-digestible oligosaccharides, particularly galacto-oligosaccharides and fructo-oligosaccharides in the present composition to further improve the present therapy in infants born via caesarean section.

TABLE 3

Percentage *Bifidobacteria* in vaginally and caesarean section delivered infants fed a formula with (GFSF) or without (SF) non-digestible oligosaccharides.

| Infants | Bifidobacteria in first week (%) | Bifidobacteria after 6 weeks (%) | Fecal pH | E. coli (%) |
|---|---|---|---|---|
| Vaginal delivery | 19.8 | | | |
| C-section SF | 4.3 | 12.3 | 7.2 | 11.8 |
| C-section GFSF | 4.3 | 17.2 | 6.5 | 0 |

Example 3

Bifidogenic Effect of Non-Digestible Oligosaccharides

Infants were administered infant formula supplemented with 0.8 g/100 ml galacto-oligosaccharides (GOS) with an average DP between 2 and 7 and fructo-oligosaccharides with (FOS, Raftilin HP®) (GFSF-group) or standard infant formula without non-digestible oligosaccharides (SF-group).

The bifidobacterial content in the feces was determined. The percentage of the genus *Bifidobacterium* as a percentage of total bacteria at 6 weeks was 47% in the SF and 68% in the GFSF group, respectively, which demonstrates that the GFSF group, fed a mixture of non-digestible carbohydrates, has a more bifidogenic flora compared to the SF group.

Also on a species level the percentage *Bifidobacterium infantis* was 22% in the GFSF group and 18% in the SF group, *B. longum* was 3.7% in the GFSF group and 2.9% in the SF group and *B. breve* was 3.7% in the GFSF group and 2.3% in the SF group. The results are indicative for the advantageous use of non-digestible neutral oligosaccharides, particularly galacto-oligosaccharides and fructo-oli-

Example 4

Composition for Babies Born Via Caesarean Section

An infant formula composition comprising per 100 ml ready to feed formula: 1.6 g protein, 3.6 g fat, 6.4 g digestible carbohydrates (mainly lactose), 0.8 g non-digestible oligosaccharides of which 0.54 g transgalacto-oligosaccharides, 0.06 g inulin, and 0.2 g pectin hydrolysate (prepared by lyase hydrolysis of citrus pectin). The package and/or supporting material accompanying the product indicates that the product can be suitably used to a) prevent and/or treat infection in infants delivered via caesarean section; b) prevent and/or treat infection with *E. coli* in infants delivered via caesarean section; c) prevent and/or treat allergy in infants delivered via caesarean section; and/or d) modulate the immune system.

Example 5

Method for Feeding Babies Born Via Caesarean Section

Sachet which contains:
0.2 g uronic acid oligosaccharide (about 2 wt. % based on dry weight);
2 g galacto-oligosaccharide and 0.3 g fructo-oligosaccharides (about 20 wt. % based on dry weight);
*Bifidobacterium breve* and *Bifidobacterium longum*, about $5*10^9$ cfu of each strain;
Bulking agent

The invention claimed is:

1. A method for stimulating the development of a healthy intestinal flora and/or decreasing the occurrence of intestinal pathogens in infants delivered via caesarean section comprising administering within 3 months of birth to the infant delivered via caesarean section a composition that is not human milk and comprises:
(a) 0.5 to 75 g of non-digestible oligosaccharides per 100 g dry weight of the composition, wherein the non-digestible oligosaccharides comprise galacto-oligosaccharides having at least 50% of its saccharide units of the galacto-oligosaccharides as galactose units, and
(b) at least one *Bifidobacterium* selected from the group consisting of *B. Longum, B. Breve, B. infantis, B. catenulatum, B. pseudocatenulatum, B. adolescentis, B. animalis, B. gallicum, B. lactis* and *B. Bifidum*.

2. The method according to claim 1, wherein the composition comprises at least one non-digestible oligosaccharide selected from the group consisting of galactooligosaccharides, non-digestible dextrins, xylo-oligosaccharides, arabino-oligosaccharides, gluco-oligosaccharides, chito-oligosaccharides, fuco-oligosaccharides, manno-oligosaccharides, isomalto-oligosaccharide, fructo-oligosaccharides, arabino-galactooligosaccharides, glucomanno-oligosaccharides and galactomanno-oligosaccharides.

3. The method according to claim 2, wherein the gluco-oligosaccharides comprise gentio-oligosaccharides and/or cyclodextrins.

4. The method according to claim 2, wherein the fructo-oligosaccharides comprise inulins.

5. The method according to claim 1, wherein the composition comprises galacto-oligosaccharides and/or fructo-oligosaccharides.

6. The method according claim 1, wherein the composition comprises a lipid component, a protein component and a carbohydrate component, wherein said lipid component provides 5 to 50% of the total calories, said protein component provides 5 to 50% of the total calories, said carbohydrate component provides 15 to 90% of the total calories.

7. The method according to claim 1, comprising at least *B. Longum* and/or *B. Breve*.

8. The method according to claim 1, comprising at least two Bifidobacteria selected from the group consisting of *B. Longum, B. Breve, B. infantis, B. catenulatum, B. pseudocatenulatum, B. adolescentis, B. animalis, B. gallicum, B. lactis* and *B. Bifidum*.

9. The method according to claim 1, wherein the composition comprises long chain polyunsaturated fatty acids and/or nucleotides.

10. The method according to claim 1, wherein the composition is administered to the infant within one week after birth, preferably within 100 hours after birth.

* * * * *